(12) United States Patent
Bennett

(10) Patent No.: US 8,895,034 B2
(45) Date of Patent: Nov. 25, 2014

(54) COLLAGEN PRODUCTION COMPOUND

(75) Inventor: Mark K. Bennett, Midlothian, VA (US)

(73) Assignee: Mark K Bennett, Midlothian, VA (US)

( * ) Notice: Subject to any disclaimer, the term of this patent is extended or adjusted under 35 U.S.C. 154(b) by 225 days.

(21) Appl. No.: 13/287,602

(22) Filed: Nov. 2, 2011

(65) Prior Publication Data

US 2013/0108603 A1     May 2, 2013

(51) Int. Cl.
| | | |
|---|---|---|
| A61K 9/14 | (2006.01) |
| A61K 8/97 | (2006.01) |
| A61K 31/198 | (2006.01) |
| A61K 36/886 | (2006.01) |
| A61Q 19/08 | (2006.01) |
| A61K 33/26 | (2006.01) |
| A61K 33/32 | (2006.01) |
| A61K 33/34 | (2006.01) |
| A61K 36/736 | (2006.01) |
| A61K 31/375 | (2006.01) |
| A61K 8/44 | (2006.01) |
| A61K 8/67 | (2006.01) |
| A61K 8/19 | (2006.01) |
| A61K 33/00 | (2006.01) |

(52) U.S. Cl.
CPC ............. *A61K 31/198* (2013.01); *A61K 36/886* (2013.01); *A61Q 19/08* (2013.01); *A61K 33/26* (2013.01); *A61K 33/32* (2013.01); *A61K 33/34* (2013.01); *A61K 36/736* (2013.01); *A61K 31/375* (2013.01); *A61K 8/44* (2013.01); *A61K 8/676* (2013.01); *A61K 8/97* (2013.01); *A61K 8/19* (2013.01); *A61K 33/00* (2013.01)
USPC .......... 424/400; 424/78.02; 424/725; 424/735

(58) Field of Classification Search
CPC ....... A61K 8/97; A61K 9/0014; A61K 36/45; A61K 36/736
USPC ............................. 424/400, 78.02, 725, 735
See application file for complete search history.

(56) References Cited

U.S. PATENT DOCUMENTS

| | | | |
|---|---|---|---|
| 4,597,762 | A | 7/1986 | Walter et al. |
| 5,747,538 | A | 5/1998 | Meybeck et al. |
| 6,426,081 | B1 * | 7/2002 | Chong .......................... 424/401 |
| 7,547,454 | B2 * | 6/2009 | Gupta .......................... 424/642 |
| 7,776,915 | B2 | 8/2010 | Morariu |
| 7,964,582 | B2 | 6/2011 | Stone et al. |
| 2002/0098213 | A1 | 7/2002 | Bonte et al. |
| 2004/0005342 | A1 | 1/2004 | Bernerd |
| 2004/0043047 | A1 | 3/2004 | Dumas et al. |
| 2004/0191330 | A1 | 9/2004 | Keefe et al. |
| 2004/0228887 | A1 | 11/2004 | Champ et al. |
| 2007/0237735 | A1 | 10/2007 | Denommee |
| 2008/0306001 | A1 | 12/2008 | Liik et al. |
| 2009/0068255 | A1 | 3/2009 | Yu et al. |
| 2010/0166897 | A1 | 7/2010 | Laboureau et al. |
| 2010/0173853 | A1 | 7/2010 | Laboureau et al. |
| 2010/0272790 | A1 | 10/2010 | Morariu |
| 2011/0045036 | A1 | 2/2011 | Lintner et al. |
| 2011/0171180 | A1 | 7/2011 | Bush et al. |
| 2011/0171286 | A1 | 7/2011 | Cecile et al. |

FOREIGN PATENT DOCUMENTS

| | | | |
|---|---|---|---|
| EP | 2389922 | A1 | 11/2011 |
| FR | 2597337 | * | 10/1987 |
| GB | 2284154 | A | 5/1995 |
| JP | 2003176232 | * | 6/2003 |
| JP | 2007031305 | * | 2/2007 |
| JP | 2010024209 | * | 2/2010 |
| WO | 9947114 | A1 | 9/1999 |
| WO | 2010082176 | A2 | 7/2010 |

* cited by examiner

*Primary Examiner* — Ruth Davis
(74) *Attorney, Agent, or Firm* — W. David Swayze, Jr.

(57) ABSTRACT

A topical skin care lotion includes materials for supplementing the production of collagen I and III includes a base of lipophillic or lipophobic material and at least one amino acid. The amino acids are alanine and glycine. Other components of the lotion include iron, vitamin C, manganese, silica and cherry fruit extract. Together, these components assist the body with the production of collagen and promote healing of damaged skin. Antioxidants are also provided to protect the skin from oxidative stress by ultraviolet sunlight and environmental hazards.

13 Claims, No Drawings

COLLAGEN PRODUCTION COMPOUND

FIELD OF THE INVENTION

The present invention relates to the protective and nutritional aspects of skin cream, and more particularly to a skin cream formulated to assist in the prevention or slowing of premature aging of skin, to reduce wrinkles, and to supplement the skin and surrounding tissues with vital nutrients that maintain skin health.

BACKGROUND OF THE INVENTION

The skin is the largest organ of the human body and receives the most exposure to the sun and chemicals in the surrounding environment. As is well known, virtually everything that is applied to the skin is absorbed by the surrounding tissue and may eventually enter the bloodstream. If appropriate nutritional elements are routinely delivered to the skin, the overall health of the skin and surrounding tissue can be improved.

Collagen is naturally produced by the human body and helps maintain the skin. Skin health and condition can be improved by supplementing or stimulating the body's natural production of collagen.

BRIEF DESCRIPTION OF THE PRIOR ART

Skin care preparations which are used to assist the body in generating collagen I and collagen II are well known in the patented prior art. For example, the Meybeck et al U.S. Pat. No. 5,747,538 discloses the use of ginsensoside $R_0$ to prepare a skin care composition for promoting collagen synthesis, particularly collagen I and collagen II.

The Morariu U.S. Pat. No. 7,776,915 teaches a topical composition for skin treatment which contains a large number of components including enzymes, acids, plant extracts and the like. The Bernerd US patent application publication No. 2004/0005342 discloses a skin care product which includes ascorbic acid. Amino acids used in an anti-aging composition are disclosed in the Denommee US patent application publication No. 2007/0237735 and hyaluronic acid compositions including vitamins for use in skin treatment are disclosed in the Cecile et al US patent application publication No. 2011/0171286.

While the prior products operate satisfactorily, most appear to contain or target production of the wrong type of collagen associated with skin. That is, they focus on collagen II which is found in cartilage, for example, rather than collagen I and III that are manufactured in the skin. In addition, it is difficult—if not impossible—for the skin to absorb a molecule the size of collagen, so very little benefit is derived from including it in existing skin care products.

The present invention was developed in order to overcome these and other drawbacks of the prior compositions by providing an additive complex lotion of various nutrients designed to deliver building blocks for assembly of collagen I and III within the skin, as well as supporting the function and repair of local cells in the areas where the lotion is applied on the skin. The lotion can be applied topically to all areas of the skin surface, including the face and neck, in order to supply skin tissue with a variety of nutrients. As these nutrients are absorbed through the skin, the natural biochemical components within the body may utilize the nutrients to support various functions related to cell protection with anti-oxidant components and to deliver the basic building blocks of collagen that can be incorporated into the skin's natural process of piecing collagen together. Other ingredients in the present invention are included to provide support and stimulation of the collagen production process itself. In addition, the nutrients help soften the skin and prevent premature aging of the skin.

SUMMARY OF THE INVENTION

Accordingly, it is a primary object of the invention to provide an anti-aging skin lotion which includes a lipophilic or lipophobic base material and at least one of alanine and glycine for assisting in the production of collagen. In a preferred embodiment, the lotion includes both alanine and glycine in generally equal amounts. Other nutrients and vitamins are provided in the lotion including iron, vitamin C, manganese, silica, and cherry fruit extract.

Preferably, the lotion includes 25-30% by volume alanine and glycine and less than 1% by volume of iron, vitamin C, manganese, silica, and cherry fruit extract.

The lotion also includes an antioxidant such as pine bark extract or resveratrol.

According to a further object of the invention, the base material comprises aloe or a sodium salt of pyrrolidone carboxylic acid.

The lotion also preferably contains at least one of alpha lipoic acid, gamma oryzanol, vitamin D-3, quercetin, vitamin K, vitamin E, co-enzyme Q-10, coconut oil, calcium, sodium, L-Arginine, L-Aspartic acid, L-Carnitine, L-Cysteine, L-Glutamic acid, L-Glutamine, L-Histidine, L-Isoleucine, L-Leucine, L-Lysine, L-Methionine, L-Phenylalanine, L-Proline, L-Serine, L-Threonine, L-Tryptophan, L-Tyrosine, and L-Valine.

According to a further embodiment, the lotion also contains trace amounts of at least one of bilberry extract, phosphatidyl serine, phosphatidyl choline, capsicum, ginseng, bioflavonoids, beta carotene, chromium picolinate, potassium, zinc, chelated calcium, elderberry, gingko biloba, Oregon grape root, turmeric, ginger, vitamin D, thiamine, avena sativa, RNA, vitamin B2, copper, omega 3-6-9 fatty acids, and selenium.

The lotion is topically applied to affected areas of the skin for treating those specific areas.

DETAILED DESCRIPTION

The invention comprises a lotion or gel that contains a specific set of ingredients that act alone and/or together to support health and well-being of human skin. Healthy skin has a smooth and supple appearance and the inventive lotion prevents and reduces wrinkles to prevent aging. The lotion supplements skin cells in localized areas via a topical application of nutritional ingredients. In addition, the lotion supports metabolic pathways and processes within the skin that promote the production of collagen I and III, elastin and other elements which slow or prevent aging of the skin as well as energizes cell productivity.

Antioxidants are provided in the lotion to protect the skin from oxidative stress by ultraviolet sunlight and environmental hazards. The elements included in the lotion are either lipophilic or lipophobic. Lipophilic elements are diluted in water whereas lipophobic elements are diluted in oil. The nature of the lotion as a base or vehicle includes ingredients that incorporate both types of elements. The inventive formula is added to a neutral or basic lotion or gel in order to aid topical application of the ingredients.

Example 1

According to a preferred embodiment of the invention, the lotion includes amino acids and specifically 28% by volume alanine and 28% by volume glycine. The right mix of amino acids acts as a complete regenerative treatment for the skin, hair and nails. It supplies vital active substances that are essential for improving hair quality, strengthening nails and increasing the skin's elasticity. Amino acids are important natural moisturizing factors in the stratum corneum. When epidermal cells die and turn into the stratum corneum, proteins in the cells are degraded to amino acids and transported to the stratum corneum. About half of the natural moisturizing factors in the skin are made up of amino acids and pyrrolidone carboxylic acid (PCA) derived from glutamate, another amino acid.

Nearly half the amino acids of collagen are alanine and glycine. Alanine is used in a wide variety of cosmetics and personal care products as a skin conditioning agent, antistatic agent and masking ingredient, and as an amino acid, combines with the epidermal cells to fill up creases, and thus provide the surface of the skin with a smoother appearance.

Approximately one-third of collagen, which keeps the skin and connective tissue firm and flexible, is composed of glycine. High amounts of glycine are also found in gelatin, which is a form of denatured collagen. Without glycine the body would not be able to repair damaged tissues, and the skin would become slack as it succumbed to ultraviolet rays, oxidation, and free radical damage, and wounds would never heal. Glycine plays a key role in the development and quality of our skeletal muscles, tissues, and structural integrity. It helps repair tissues. Because glycine is a component of glucose tolerance factor and of the enzyme glutathione which are found in high concentrations in the skin and connective tissues, it is useful for repairing damaged tissues and promoting healing. It also speeds the healing of wounds.

The lotion also contains 0.01% by volume of iron and 0.3% by volume of vitamin C. The iron is preferably chelated iron. In the process of collagen synthesis, one of the first modifications to occur is hydroxylation of selected proline and lysine amino acids in the newly synthesized pro-collagen protein. Specific enzymes called hydroxylases are responsible for these important reactions which are necessary to form hydroxyproline and hydroxylysine. The hydroxylase enzymes require vitamin C and iron as cofactors.

Chelated iron is simply iron that has undergone chelation, a chemical process that firmly binds the iron molecule to another substance, usually an amino acid. This forms a more stable ring-shaped molecule that is easier for plants and animals to absorb. Cells have membranes which allow some substances to pass through, while blocking others. Chelated iron, disguised as an amino acid, is thought to pass through the cell membrane more easily, allowing the iron inside the cell where it is needed. Iron is also involved in elastin and collagen production.

Vitamin C is an antioxidant that slows the rate of free-radical damage. Free radicals are unstable molecules that damage collagen and cause skin dryness, fine lines and wrinkles. Vitamin C, also known as ascorbic acid, is important to the production of collagen, a protein that aids in the growth of cells and blood vessels and gives skin its firmness and strength. Vitamin C is also applied to the skin to protect against sun, pollutants, and radiation. Ultraviolet rays from the sun break down collagen, which leads to increased wrinkles. Vitamin C also plays a role as a natural anti-inflammatory to inhibit the onset of aging in the skin.

The lotion according to the preferred embodiment of the invention also includes 0.006% by volume of manganese, 0.3% by volume of silica, and 0.4% by volume of cherry fruit extract.

In the process of collagen synthesis, some of the formed hydroxylysine amino acids are glycosylated by the addition of sugars, such as galactose and glucose. The enzymes that catalyze the glycosylation step, galactosyl and glucosyl transferases, require the trace metal manganese. Manganese (AA chelated) is a mineral found in large quantities in both plant and animal matter. Only trace amounts of this element can be found in human tissue. Manganese is a component of the antioxidant enzyme manganese superoxide dismutase (MnSOD). Antioxidants scavenge damaging particles in the body known as free radicals. These particles occur naturally in the body but can damage cell membranes, interact with genetic material, and contribute to the aging process as well as the development of a number of health conditions. Antioxidants such as MnSOD neutralize free radicals and reduce or help prevent some of the damage they cause.

Silica is an essential element found in the earth's crust. This trace mineral is rare in human diets because food is processed and soil is depleted by chemical treatments. Silica is known to slow the aging process. Collagen is composed primarily of silica and the addition of silica to the body enhances collagen production allowing humans to retain a youthful appearance. The presence of silica in the body also maintains the luster in hair, strengthens nails, and maintains skin tone.

Cherry fruit extract contains flavonoids which act as antioxidants in the body, degenerating and destroying harmful oxygen compounds generally referred to as free radicals. Free radicals are responsible for many critical diseases. Cherry extract strengthens capillaries because the flavonoids found therein strengthen collagen, the building fibers of connective tissue. Cherry extract facilitates cross-linking of fibers themselves, by providing additional flavonoids. This process repeats itself resulting in a web of connective tissues that include tendons, cartilage, and other key structural tissues. Cherry extract also helps strengthen the collagen fibers that are the basic structure of the vein wall. Extracts of cherries and blueberries have been frequently used in Europe for the treatment of varicose veins. Cherries contain high quantities of vitamins A, C, D and K, thiamin, riboflavin, niacin, vitamin B6, folate, vitamin B12, panthothenic acid, choline and betaine. Cherries are also rich in many minerals including calcium, iron, magnesium, phosphorus, potassium, sodium, zinc, copper, manganese, selenium and fluoride. Moreover, cherries are very low in saturated fat but have high concentrations of omega 3 and omega 6 fatty acids, which are known to be of health benefit to humans. Cherries contain no cholesterol, no caffeine and no theobromine. They are believed to slow the aging process, and improve hair, skin and nails.

Supplements

The lotion according to the invention may be provided with additional nutrients and supplements to support metabolism within the skin. These will be now be described, together with the benefits provided by each.

A preferred nutritional supplement is 0.20% by volume of choline. Although humans synthesize choline in small amounts, the body does not produce a sufficient amount for skin health. Most of the choline in the human body is located in phosphatidylcholine. Choline and the compounds derived from it serve many vital functions. It is used in the synthesis structural components of all human cell membranes. Choline containing phospholipids, phosphatidylcholine and sphingomyelin are precursors for the intracellular messenger molecules diacylglycerol and ceramide. Choline is used to make cell signaling molecules, platelet activating factors and sphingophosphorylcholine. It is also a precursor for an important neurotransmitter, involved in muscle control, memory, and many other functions. Choline also assists with stabilizing silica, as well as cell transport and inflammation response.

Another supplement for the lotion according to the invention is 0.03% pine bark extract, one of the most powerful antioxidants and a potent anti-inflammatory. Antioxidants function to protect the body from free radicals which are unstable molecules that harm tissues and DNA and contribute to both aging and the development of a variety of diseases. Ultraviolet radiation from sunlight generates a large amount of free radicals that damage skin cells and the structural components of skin causing photo-aging of the skin (i.e. wrinkles, lines, loss of elasticity, and pigmentation changes) as well as some types of skin cancer. Antioxidants, such as vitamin C, vitamin E, pine bark extract, and many others are the body's natural defense against free radicals. They deactivate free radicals, thereby preventing them from causing harm. As an antioxidant, pine bark extract provides two levels of antioxidant protection for skin. First, pine bark extract scavenges free radicals, outperforming a variety of antioxidants including vitamins E and C, co-enzyme Q10, and lipoic acid. Secondly, pine bark extract works synergistically with other antioxidants by improving the functioning of vitamin C, protecting vitamin E from degradation, and increasing the amount of some natural antioxidants produced by the body. By outperforming other antioxidants and enhancing the function of other essential antioxidants, pine bark extract provides superior antioxidant protection for the skin.

Another antioxidant in the inventive lotion is 0.04% resveratrol. Resveratrol is a powerful antioxidant seen in many plants such as red grapes and peanuts. The antioxidant benefits of resveratrol help to slow the process of aging by scavenging the damage causing free radicals from the body. The free radicals would damage the cells and tissues of the body resulting in wrinkles and cell fatigue.

Free radicals are highly reactive unpaired electrons that weaken the other molecules of the body and can set off more free radicals, essentially a chain reaction, leaving the body aged and weak. Resveratrol plays a key role in anti-aging skin care because it thwarts free radical damage, making the skin smooth and soft. It also enhances circulation by improving cardio-muscular health, which in turn results in smooth and wrinkle free skin.

Topical application of resveratrol is useful in the cases of skin cancer and other skin ailments. Ultraviolet rays, pollution and stress are some of the common causes for skin damage. These factors cause the oxidation of cell molecules which set off free radicals, which in turn destroy the collagen of the skin. Collagen is what offers the support for the skin tissue by holding it in place without sagging. As the body ages, the skin starts to lose its elasticity due to the deficiency of collagen, which results in cosmetic imperfections such as dark circles and crow's feet. With the application of facial creams containing resveratrol, the aging process can by reversed by making the skin smooth and wrinkle free. Resveratrol also enhances the capillary circulation in the tissues making it smooth and healthy.

A further supplement to the inventive lotion is 0.01% by volume of alpha lipoic acid, a well-known natural substance found in certain foods and also produced in the human body. It has an impressive array of potentially beneficial mechanisms of action and is a potent and versatile antioxidant. It directly recycles vitamin C, indirectly recycles vitamin E, and is a co-factor in a key biochemical pathway responsible for energy production in the cells. It inhibits cross-linking which is the formation of chemical bridges between proteins or other large molecules. Cross-linking contributes to the aging process by causing hardening of arteries, wrinkling of the skin and stiffening of joints. Lipoic acid has a moderate anti-inflammatory effect and it has the capacity to neutralize and remove a variety of toxic metals from the body.

All of the above effects of lipoic acid benefit skin cells and thus improve skin texture and wrinkles.

Two other ingredients in the lotion are 0.02% by volume of gamma oryzanol and 0.10% by volume of quercetin.

Gamma oryzanol is a natural nutrient extract isolated from rice bran oil that contains a mixture of sterols and ferulic acids which aid in the destruction of free radicals in the skin. It slows the progress of melanin pigmentation by intercepting the ultraviolet rays at the skin's surface and hinders their transmission. Gamma oryzanol is often seen in sunscreen. It is also able to protect skin lipids from oxidation, and is used to prevent freckles, age spots, and darkening of the skin. Gamma oryzanol is recognized as an effective nutrient because it is oil soluble, easily absorbed into the skin and has the effect of stimulating blood circulation under the skin. According to a recent study where the lipid peroxidation of linoleic acid was measured after exposure to UV light with and without 1% gamma oryzanol, peroxidation was suppressed indicating that topical gamma oryzanol has the ability to prevent some of the damage to skin caused by sunlight. This and other studies suggest that gamma oryzanol helps to maintain skin function by improvement of skin microcirculation, protection against lipid peroxidation and direct stimulation of sebaceous gland function. With continuous use, it prevents some aspects of skin aging for long periods of time.

Quercetin is a type of flavonoid that serves as the backbone for many other members of the flavonoid family, including the citrus flavonoids rutin, quercitrin, and hesperidin. Flavonoids, or bioflavonoids, are plant pigments that provide fruits, flowers, and vegetables much of their color. Quercetin is primarily found in citrus fruits, apples, onions, parsley, tea, and red wine. There are thousands of different flavonoids and those such as quercetin provide many powerful health-promoting benefits. Quercetin, along with other flavonoids, can also improve the health of capillaries. In addition, quercetin, along with other flavonoids, improves the health of connective tissues, thus alleviating bruising, edema, varicose veins, and fragile capillaries.

The lotion may also include 0.00002% by volume vitamin D3, 0.00003% by volume vitamin K, and 0.20% by volume vitamin E. Vitamin D3, or cholecalciferol (clinical/molecular formula: $C_{27}H_{44}O$), is naturally manufactured in the skin, primarily through exposure to sunlight. Vitamin D3 helps rejuvenate the skin and is used by women to get rid of stretch marks. Vitamin D3 also plays a role as a natural anti-inflammatory. Inflammation of tissue may contribute to the increased onset of aging in the skin.

Vitamin K is a fat-soluble vitamin which is useful for the normal coagulation of blood. Vitamin K allows certain proteins to bind calcium which is essential for good bone mineralization. Vitamin K also plays a very important role in your overall facial rejuvenation strategy by improving skin value, promoting healing of skin discolorations, and improving the healing and appearance of scars and other skin imperfections Vitamin E is a natural antioxidant that is naturally hydrating and has clinically proven skin-healing properties. Vitamin E can be used topically making it effective for repairing damaged and dry skin.

Another ingredient for the lotion is 0.10% co-enzyme Q10 which has strong antioxidant properties and contributes to the production of cell energy. In the citric acid cycle, co-enzyme Q10 is utilized in a step in the overall process that ultimately results in an output of more cell fuel. It supports a process that generates usable fuel for that particular cell and therefore supports overall health and energy of a cell and cellular activities.

Another ingredient that may be included in the lotion is 41% by volume coconut oil which acts as an effective moisturizer on all types of skin including dry skin. The benefit of coconut oil on the skin is comparable to that of mineral oil. Further, unlike mineral oil, there is no chance of having any adverse side effects on the skin with the application of coconut oil. Coconut oil therefore is a safe solution for preventing dryness and flaking of skin. It also delays wrinkles, and sagging of skin which normally becomes prominent with age. Coconut oil also helps treat various skin problems including psoriasis, dermatitis, eczema and other skin infections. It prevents premature aging and degenerative diseases due to its antioxidant properties. The small molecular structure of coconut oil allows for easy absorption through the skin resulting in a soft, smooth texture. It makes an ideal ointment for the relief of dry, rough and wrinkled skin.

The base or carrier material for the lotion comprises 1 ml of liquid sodium salt or aloe gel. The preferred sodium salt is NaPCA, pyrrolidone carboxylic acid, a natural skin moisturizer. Older skin contains only about half the amount of NaPCA found in young skin. The ability of skin to hold moisture is directly related to its NaPCA content. It is water, and not oil, that keeps skin soft and supple. NaPCA pulls water out of the air, moisturizing the skin, improving its appearance, and giving it a moist and youthful glow.

Aloe may be used as the base material because of its ability to soothe and stimulate skin cell renewal, as well as stimulate fibroblast production which is responsible for collagen production.

In addition, all hydrophobic compounds according to the invention are absorbed into approximately 0.5 ml of Omega 3-6-9 oil.

Fiji brand water is a preferred carrier material for the lotion because it contains trace amounts of silica. In addition, trace amounts of the following compounds may be present in solution from other sources: silica, gelatin, egg white hydrolysate, L-tartrate, polyethylene glycol, maltodextrin, cellulose, stearic acid, colloidal silicone dioxide, sorbitol, magnesium stearate, monolaurin, eucalyptus, ethanol, rice flour, MCT, olive oil, rosemary extract, wheat germ oil, ascorbic palmitate, titanium dioxide, soybean oil, and glycerin. None of these compounds are of primary significance to the inventive lotion. However, all of these compounds play a secondary and supportive role in supporting skin health.

Other nutrients which may be provided in the lotion and the percentage by volume of each are calcium (0.01%), sodium (0.001%), L-arginine (0.01%), L-aspartic acid (0.08%), L-carnitine (0.003%), L-cysteine (0.02%), L-glutamic acid (0.10%), L-glutamine (0.03%), L-histidine (0.01%), L-isoleucine (0.05%), L-leucine (0.07%), L-lysine (0.07%), L-methionine (0.01%), L-phenylalanine (0.01%), L-proline (0.04%), L-serine (0.03%), L-threonine (0.05%), L-tryptophan (0.01%), L-tyrosine (0.01%) and L-valine (0.04%).

Additional Supplements

A number of other ingredients may be included in alternate embodiments of the lotion according to the invention. These include:
  billberry extract—contains polyphenols and anthocyanidins, which possess antioxidant properties and which helps to increase quercitin, improve blood flow, and strengthen collagen;
  phosphatidyl serine—a natural occurring fat molecule that can slows skin aging and prevents collagen reduction;
  phosphatidyl choline—assists in communication and repair of cell membranes throughout the body, including within the skin, and assists with manufacturing and repairing cell membranes;
  capsicum—in small amounts warms and stimulates the skin temporarily in the applied areas;
  ginseng—maintains elasticity and regenerative capacity of mature skin;
  bioflavonoids—includes antioxidant properties, promotes circulation and works with Vitamin C to protect collagen and elastin in the dermis layer of skin;
  beta carotene—includes antioxidant properties, restores suppleness, evens out skin tone and protects skin from sun damage;
  chromium picolinate—lowers sugar levels to prevent a dull and wrinkled appearance;
  potassium—prevents dry skin;
  zinc—provides sun protection, skin cell repair and restores firmness and elasticity to the skin;
  calcium (chelated)—regulates enzymes and operation of cell membranes;
  elderberry—includes antioxidant and anti-inflammatory properties;
  gingko biloba—improves circulation and increases collagen production;
  oregon grape root—prevents dry skin;
  turmeric—includes anti-inflammatory properties;
  ginger—includes anti-inflammatory properties;
  vitamin D—includes anti-inflammatory properties;
  thiamine—regulates proper cell function in skin by promoting hydration;
  avena sativa—includes antioxidant and emollient properties;
  RNA—reduces wrinkling, improves elasticity, and supports genesis of mitrochondria in cells, which would result in increased cell energy production on localized area;
  vitamin B2—maintains healthy skin and metabolizes fat;
  copper—produces collagen and elastin and restores firmness and elasticity to the skin;
  omega 3-6-9 fatty acids—used in the formation of cell walls, making them supple and flexible, and acts as an anti-inflammatory to delay the onset of aging in the skin; and
  selenium—acts as an antioxidant and an anti-inflammatory to delay the onset of aging in the skin.

While the preferred forms and embodiments of the invention have been described, it will be apparent to those of ordinary skill in the art that various changes and modifications may be made without deviating from the inventive concepts set forth above.

What is claimed is:

1. An anti-aging skin lotion which promotes the production of collagen, comprising
   (a) at least one of a lipophillic and lipophobic base material; and
   (b) an amino acid comprising equal amounts of alanine and glycine in the range of 25-30% by volume;
   (c) chelated iron; and
   (d) vitamin C.

2. An anti-aging skin lotion as defined in claim 1 and further comprising manganese.

3. An anti-aging skin lotion as defined in claim 2, and further comprising silica.

4. An anti-aging skin lotion as defined in claim 3, and further comprising cherry fruit extract.

5. An anti-aging skin lotion as defined in claim 4, wherein the amounts of iron, vitamin C, manganese, silica, and cherry fruit extract are less than 1% by volume.

6. An anti-aging skin lotion as defined in claim 5, and further comprising at least one antioxidant.

7. An anti-aging skin lotion as defined in claim 6, wherein said antioxidant comprises at least one of pine bark extract and resveratrol.

8. An anti-aging skin lotion as defined in claim 6, and further comprising choline.

9. An anti-aging skin lotion as defined in claim 8, wherein said base material comprises aloe.

10. An anti-aging skin lotion as defined in claim 8, wherein said base material comprises a sodium salt of pyrrolidone carboxylic acid.

11. An anti-aging skin lotion as defined in claim 8, and further comprising at least one of alpha lipoic acid, gamma oryzanol, vitamin D-3, quercetin, vitamin K, vitamin E, co-enzyme Q-10, coconut oil, calcium, sodium, L-Arginine, L-Aspartic acid, L-Carnitine, L-Cysteine, L-Glutamic acid, L-Glutamine, L-Histidine, L-Isoleucine, L-Leucine, L-Lysine, L-Methionine, L-Phenylalanine, L-Proline, L-Serine, L-Threonine, L-Tryptophan, L-Tyrosine, and L-Valine.

12. An anti-aging skin lotion as defined in claim 11, and further comprising trace amounts of at least one of bilberry extract, phosphatidyl serine, phosphatidyl choline, capsicum, ginseng, bioflavonoids, beta carotene, chromium picolinate, potassium, zinc, chelated calcium, elderberry, gingko biloba, Oregon grape root, turmeric, ginger, vitamin D, thiamine, avena sativa, RNA, vitamin B2, copper, omega 3-6-9 fatty acids, and selenium.

13. A skin lotion to prevent aging and promote collagen production within the skin, comprising
 (a) a base material of one of a lipophillic and lipophobic material;
 (b) 28% of alanine;
 (c) 28% of glycine;
 (d) 0.01% of chelated iron;
 (e) 0.3% of vitamin C;
 (f) 0.006% of manganese;
 (g) 0.3% of silica; and
 (h) 0.4% of cherry fruit extract.

* * * * *